United States Patent [19]

Xu

[11] Patent Number: 6,027,929

[45] Date of Patent: Feb. 22, 2000

[54] **METHOD FOR CLONING AND PRODUCING THE NSPI RESTRICTION ENDONUCLEASE IN *E. COLI* AND PURIFICATION OF THE RECOMBINANT NSPI RESTRICTION ENDONUCLEASE**

[75] Inventor: Shuang-yong Xu, Lexington, Mass.

[73] Assignee: New England Biolabs, Inc., Beverly, Mass.

[21] Appl. No.: 09/135,782

[22] Filed: Aug. 18, 1998

[51] Int. Cl.[7] .............................. C12N 9/22; C12N 15/55
[52] U.S. Cl. ................... 435/199; 435/252.3; 435/320.1; 536/23.2
[58] Field of Search ................ 435/199, 320.1, 435/252.3; 536/23.2

[56] References Cited

U.S. PATENT DOCUMENTS 5,200,333  4/1993  Wilson .................................. 435/172.7
5,498,535  3/1996  Fomenkov et al. ................... 435/172.3

OTHER PUBLICATIONS

Roberts et al, Nucl. Acids Res. 26:338–350 (1998).
Kosykh et al., Mol. Gen. Genet. 178:717–719 (1980).
Mann et al., Gene 3:97–112 (1978).
Walder et al., Proc. Nat. Acad. Sci. 78:1503–1507 (1981).
Bouqueleret et al., Nucl. Acids. Res. 12:3659–3676 (1984).
Gingeras et al., Proc. Natl. Acad. Sci. USA 80:402–406 (1983).
Theriault et al., Gene 19:355–359 (1982).
Blumenthal et al., J. Bacteriol. 164:501–509 (1985).
Wayne et al., Gene 195:321–328 (1997).
Kiss et al., Nucl. Acids. Res. 13:6403–6421 (1985).
Szomolanyi et al., Gene 10:219–225 (1980).
Janulatis et al., Gene 20:197–204 (1982).
Kiss et al., Gene 21:111–119 (1983).
Walder et al., J. Biol. Chem. 258:1235–1241 (1983).
Fomenkov et al., Nucl. Acids Res. 22:2399–2403 (1994).
Skoglund et al., Gene 88:1–5 (1990).
Xu, S–Y., et al. (1998) 260, 226–231.

*Primary Examiner*—Charles L. Patterson, Jr.
*Attorney, Agent, or Firm*—Gregory D. Williams

[57] ABSTRACT

The present invention relates to clones which express the recombinant NspI restriction endonuclease using a NspI methylase premodified *E. coli* K strain RR1 (λDE3) and to methods for producing and purifying said enzyme.

6 Claims, 4 Drawing Sheets

```
       ATGCAAGGTACACAACTTTCTTTTTTTAGCAACGAAGAAGGGTTTAATCCTACCAAAAAG
  1    ---------+---------+---------+---------+---------+---------+
       M  Q  G  T  Q  L  S  F  F  S  N  E  E  G  F  N  P  T  K  K
       GAGAAAAAACCAAAATTAGGACGTTATGAACGTATCAAACGTAATTTAGAGAAAAATGAT
  61   ---------+---------+---------+---------+---------+---------+
       E  K  K  P  K  L  G  R  Y  E  R  I  K  R  N  L  E  K  N  D
       CAAGATCCATACAAGATATTTATTGATGTTAATACCCCACTAATACCAGCATCTCAATAT
  121  ---------+---------+---------+---------+---------+---------+
       Q  D  P  Y  K  I  F  I  D  V  N  T  P  L  I  P  A  S  Q  Y
       ACTTTTGTGGATCTGTTCTGTGGTGCAGGAGGAATTACACAAGGATTAGTACAGGCTGGA
  181  ---------+---------+---------+---------+---------+---------+
       T  F  V  D  L  F  C  G  A  G  G  I  T  Q  G  L  V  Q  A  G
       TTCCAGGCCTTAGCTAGTGTGGAAATTAGTCCAATTGCTTCTGCTACACATCAAAGAAAT
  241  ---------+---------+---------+---------+---------+---------+
       F  Q  A  L  A  S  V  E  I  S  P  I  A  S  A  T  H  Q  R  N
       TTTCCTCATTGTCATCATTTTTGGGGAGATATAGAACAATTTTATCCAAAAAGTTGGTTG
  301  ---------+---------+---------+---------+---------+---------+
       F  P  H  C  H  H  F  W  G  D  I  E  Q  F  Y  P  K  S  W  L
       CAACAAATTGGCTATCCTGAAGTAAATCTGGTGGTTGGTGGTCCTCCTTGTCAGGGGTTT
  361  ---------+---------+---------+---------+---------+---------+
       Q  Q  I  G  Y  P  E  V  N  L  V  V  G  G  P  P  C  Q  G  F
       TCGGTAGCAGGTAAACGCGATCCCAAAGATCCGCGTAATCGTCTATTTTATGAATTTGTA
  421  ---------+---------+---------+---------+---------+---------+
       S  V  A  G  K  R  D  P  K  D  P  R  N  R  L  F  Y  E  F  V
       CGTGTGGTATCAGAAATACGTCCGTGGTATGTAGTTATGGAAAATGTACCAGGAATTCTA
  481  ---------+---------+---------+---------+---------+---------+
       R  V  V  S  E  I  R  P  W  Y  V  V  M  E  N  V  P  G  I  L
       ACCATTCAAAATGGAAATGTGAAGCAAGCTATTATTGAAGCTTTTGAATCTATTGGTTAT
  541  ---------+---------+---------+---------+---------+---------+
       T  I  Q  N  G  N  V  K  Q  A  I  I  E  A  F  E  S  I  G  Y
       CCTCATGTTTCTGTAGCAATTCTAGAATCTGCTGACTATGGAGTACCACAGATTAGACCA
  601  ---------+---------+---------+---------+---------+---------+
       P  H  V  S  V  A  I  L  E  S  A  D  Y  G  V  P  Q  I  R  P
       AGAGCTATCTTTATTGCTAATAGATTCGGAATGCCAAATCCATATCCTAAAGCTCAGTTA
  661  ---------+---------+---------+---------+---------+---------+
       R  A  I  F  I  A  N  R  F  G  M  P  N  P  Y  P  K  A  Q  L
       TTACCAGAAGAATATAAACCCATCGAATCAGCTATTTCTGATTTACCAGAATATACTCCA
  721  ---------+---------+---------+---------+---------+---------+
       L  P  E  E  Y  K  P  I  E  S  A  I  S  D  L  P  E  Y  T  P
       ATTCCAGAAATTAATCACCAATGGACTAGACATTCACCAGAGTATATGGAGCGTATTGCA
  781  ---------+---------+---------+---------+---------+---------+
       I  P  E  I  N  H  Q  W  T  R  H  S  P  E  Y  M  E  R  I  A
       AAAGTACCCCCTGGTGGTTCTTTATATCAAAAATATGTTGATGCCTTTAAGCGTCAATAT
  841  ---------+---------+---------+---------+---------+---------+
       K  V  P  P  G  G  S  L  Y  Q  K  Y  V  D  A  F  K  R  Q  Y
       CCAGGTAAACCAAGTATGACTGTTAAAGAAAATCATGGCGGTACTCATATCCACCCATAT
  901  ---------+---------+---------+---------+---------+---------+
       P  G  K  P  S  M  T  V  K  E  N  H  G  G  T  H  I  H  P  Y
       TTAAATCGGGTAATTTCATCTCGTGAGATGGCAAGATTACAAAGCTTTCCTGATTCATTC
  961  ---------+---------+---------+---------+---------+---------+
       L  N  R  V  I  S  S  R  E  M  A  R  L  Q  S  F  P  D  S  F
       ATTTTTGAAGGGACTATGAAAAAAGCCATGTGGCAAATTGGGAATGCAGTCCCACCTCGT
  1021 ---------+---------+---------+---------+---------+---------+
       I  F  E  G  T  M  K  K  A  M  W  Q  I  G  N  A  V  P  P  R
       TTAGCAGAGTGTATTGGTTATGCGCTCATACCTTATTTAAACAAGATTGCACTTAACACT
  1081 ---------+---------+---------+---------+---------+---------+
       L  A  E  C  I  G  Y  A  L  I  P  Y  L  N  K  I  A  L  N  T
       GATCATCAAGTTGATATTACTTATGTTGATCAGACTGAGATAGTTTTTGATTGA
  1141 ---------+---------+---------+---------+----          1194
       D  H  Q  V  D  I  T  Y  V  D  Q  T  E  I  V  F  D  *
```

FIG. 3

```
      GTGAGCAAGGAACAAAATTTAGTACAGACAATTCAGAGCCAGTTCAGACAAGATTCAACT
  1   ---------+---------+---------+---------+---------+---------+
       M  S  K  E  Q  N  L  V  Q  T  I  Q  S  Q  F  R  Q  D  S  T
      CAACTACAAGTCTTTAAGCTGTTGTCAGATCAACAATGGCACTGTAGAGAGTGTGAAGGA
 61   ---------+---------+---------+---------+---------+---------+
       Q  L  Q  V  F  K  L  L  S  D  Q  Q  W  H  C  R  E  C  E  G
      AAGAAAATAGGATCAAATCAGTACGCTGGTGGTGGAGGTATTCAGGGATTACAACGTGGA
121   ---------+---------+---------+---------+---------+---------+
       K  K  I  G  S  N  Q  Y  A  G  G  G  I  Q  G  L  Q  R  G
      ACAAGGAGTCGTCCTGGTCTTGTAATTGAAACAACCAAAAACTACTGTCAAACTTGTCAG
181   ---------+---------+---------+---------+---------+---------+
       T  R  S  R  P  G  L  V  I  E  T  T  K  N  Y  C  Q  T  C  Q
      CAGACACGCTTAGGAGATAGGTGGACAGGTGAGATAAAATCAGCTAATTCTGCATCAAAT
241   ---------+---------+---------+---------+---------+---------+
       Q  T  R  L  G  D  R  W  T  G  E  I  K  S  A  N  S  A  S  N
      ATACCCGCTTCTTTAGTCGAAAAAATTTTACAAGTTTATTCTTATACAGATGTAATAGAA
301   ---------+---------+---------+---------+---------+---------+
       I  P  A  S  L  V  E  K  I  L  Q  V  Y  S  Y  T  D  V  I  E
      CAAAGGCAAAGAGAGAAACATGAATTAGTAATTGATCATAGATTTCCGATGGAAAGATGG
361   ---------+---------+---------+---------+---------+---------+
       Q  R  Q  R  E  K  H  E  L  V  I  D  H  R  F  P  M  E  R  W
      GGAGCTAGTGAGCCTCCACACTTAACATCTATGAATGATAATGAAATCAAGCGAAAGTTT
421   ---------+---------+---------+---------+---------+---------+
       G  A  S  E  P  P  H  L  T  S  M  N  D  N  E  I  K  R  K  F
      CAATTGTTGAAGAAAGATACCTCTGGCAATCACAATCTTTTAAAATCAAGAAGCTGTGAG
481   ---------+---------+---------+---------+---------+---------+
       Q  L  L  K  K  D  T  S  G  N  H  N  L  L  K  S  R  S  C  E
      CGATGTATCAAAACTGGTAAACGAGGTGCGCCTTTCGGGATTCATTTTTGGTATCAAGGA
541   ---------+---------+---------+---------+---------+---------+
       R  C  I  K  T  G  K  R  G  A  P  F  G  I  H  F  W  Y  Q  G
      GATGAAAACTGGCCTTCTGTACATCAGCGTGGTGATGAAGCTGAAGAAGGTTGTGTCGGA
601   ---------+---------+---------+---------+---------+---------+
       D  E  N  W  P  S  V  H  Q  R  G  D  E  A  E  E  G  C  V  G
      TGTGGTTGGTATAATTTTGAAGCGTGGCGTAATGCGCTCAATCAAAAACTATCTCAGTCT
661   ---------+---------+---------+---------+---------+---------+
       C  G  W  Y  N  F  E  A  W  R  N  A  L  N  Q  K  L  S  Q  S
      GATCAACATAAGTAA
721   ---------+-----  735
       D  Q  H  K  *
```

METHOD FOR CLONING AND PRODUCING THE NSPI RESTRICTION ENDONUCLEASE IN *E. COLI* AND PURIFICATION OF THE RECOMBINANT NSPI RESTRICTION ENDONUCLEASE

BACKGROUND OF THE INVENTION

The present invention relates to recombinant DNA which encodes the NspI restriction endonucleases as well as NspI methylases, the production of NspI restriction endonuclease from the recombinant DNA, and purification of the recombinant NspI from *E. coli* cell extract.

Type II restriction endonucleases are a class of enzymes that occur naturally in bacteria. When they are purified away from other bacterial components, restriction endonucleases can be used in the laboratory to cleave DNA molecules into small fragments for generating recombinant DNA molecules.

Restriction endonucleases act by recognizing and binding to particular sequences of nucleotides along the DNA molecule. Once bound, they cleave the molecule within, to one side of, or to both sides of the recognition sequence. Different restriction endonucleases have affinity for different recognition sequences. Over two hundred and twenty restriction endonucleases with unique specificities have been identified among the many hundreds of bacterial species that have been examined to date (Roberts and Macelis, *Nucl. Acids Res.* 26:338–350 (1998)).

Restriction endonucleases typically are named according to the bacteria from which they are derived. Thus, the species *Deinococcus radiophilus* for example, produces three different restriction endonucleases, named DraI, DraII and DraIII. These enzymes recognize and cleave the sequences 5'TTTAAA3', 5'PuGGNCCPy3' and 5'CACNNNGTG3' respectively. *Escherichia coli* RY13, on the other hand, produces only one enzyme, EcoRI, which recognizes the sequence 5'GAATTC3'.

A second component of bacterial restriction-modification (R-M) systems are the methylases. These enzymes provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is fully modified and it is therefore completely insensitive to the presence of the endogenous restriction endonuclease. It is only unmodified, and therefore identifiably foreign DNA, that is sensitive to restriction endonuclease recognition and cleavage.

With the advent of recombinant DNA technology, it is now possible to clone genes and overproduce the enzymes in large quantities. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are cloned by a number of methods. The first cloned systems used bacteriophage infection as a means of selecting restriction endonuclease clones (EcoRII: Kosykh et al., *Mol. Gen. Genet.* 178:717–719 (1980); HhaII: Mann et al., *Gene* 3:97–112 (1978); PstI: Walder et al., *Proc. Nat. Acad. Sci.* 78:1503–1507 (1981)). Since the presence of restriction-modification systems in bacteria enable them to resist infection by bacteriophages, cells that carry cloned restriction-modification genes can, in principle, be selectively isolated as survivors from libraries that have been exposed to bacteriophages. However, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acids. Res.* 12: 3659–3676 (1984); PaeR7: Gingeras and Brooks, *Proc. Natl. Acad. Sci. USA* 80:402–406 (1983); Theriault and Roy, *Gene* 19:355–359 (1982); PvuII: Blumenthal et al., *J. Bacteriol.* 164:501–509 (1985); Tsp45I: Wayne and Xu, *Gene* 195:321–328 (1997)).

A third approach, the selection for an active methylase gene has been used to clone a large number of R-M systems (U.S. Pat. No. 5,200,333 (1993) and BsuRI: Kiss et al., *Nucl. Acids. Res.* 13:6403–6421 (1985)). Since R-M genes are organized in close proximaty to each other, both genes can often be cloned simultaneously. This selection does not always yield a complete restriction system however, but instead yields only the methylase gene (BspRI: Szomolanyi et al., *Gene* 10:219–225 (1980); BcnI: Janulaitis et al., *Gene* 20: 197–204 (1982); BsuRI: Kiss and Baldauf, *Gene* 21:111–119 (1983); and MspI: Walder et al., *J. Biol. Chem.* 258:1235–1241 (1983)).

A more recent method, the "endo-blue method", has been described for direct cloning of restriction endonuclease genes in *E. coli* based on the indicator strain of *E. coli* containing the dinD: :lacZ fusion (Fomenkov et al., U.S. Pat. No. 5,498,535 (1996); Fomenkov et al., *Nucl. Acids Res.* 22:2399–2403 (1994)). This method utilizes the *E. coli* SOS response following DNA damages caused by restriction endonucleases or non-specific nucleases. A number of thermostable nuclease genes (TaqI, Tth111I, BsoBI, Tf nuclease) have been cloned by this method (U.S. Pat. No. 5,498,535 (1996)).

Because purified restriction endonucleases, and to a lesser extent, modification methylases, are useful tools for creating recombinant molecules in the laboratory, there is a commercial incentive to obtain bacterial strains through recombinant DNA techniques that produce these enzymes in large quantities. Such overexpression strains would also simplify the task of enzyme purification.

SUMMARY OF THE INVENTION

In accordance with the present invention there is provided a clone containing the gene coding for NspI restriction endonuclease derived from Nostoc sp. (ATCC 29411). The present invention also relates to clones which express recombinant NspI restriction endonuclease and NspI methylase and to methods for producing said enzymes.

NspI is an enzyme which recognizes the DNA sequence 5' RCATG^Y 3' and cleaves between the fifth and sixth bases on both strands leaving a 4 base 3' extension. NspI restriction endonuclease produced in accordance with the present invention is substantially pure and free of the contaminants normally found in NspI preparations made by conventional techniques from the native strain. The native Nostoc sp. (ATCC 29411) produces five restriction endonucleases NspI, NspII, NspIII, NspIV, and NspV. By cloning the NspI R-M system in E. coli, one can avoid the possible contamination of NspII, NspIII, NspIV, and NspV.

In accordance with the present invention, the cloning of DNA encoding the NspI modification methylase and a portion of the nspIR was achieved by methylase selection and DNA sequencing of the nspIM gene as well as the adjacent DNA. The rest of the nspIR gene was isolated by inverse PCR of the adjacent DNA to the partial open reading frame (ORF). In order to premodify E. coli host DNA, the nspIM gene was amplified by PCR and cloned in a compatible plasmid pACYC184 to generate pACYC-NspIM. The nspIR gene was amplified by PCR and cloned in a pUC19 based vector pRRS. This clone, however, was not stable due to the constitutive expression of NspI. To construct a stable overexpression clone, the nspIM gene was first cloned in pBR322 and the nspIR gene was cloned in a T7 expression vector pACYC-T7. The expression host was ER2504 [pBR-NspIM, pACYC-T7-NspIR]. This strain, however, was not stable.

While not wishing to be bound by theory, the instability was probably caused by the NspI methylase rather than NspI endonuclease (due to methylation-dependant restriction). A further attempt to overcome the stability problem, the plasmid containing M.NspI was transferred into an E. coli K strain RR1($\lambda$DE3) to generate strain RR1($\lambda$DE3) [pBR-NspIM] and a second plasmid pACYC-T7-NspIR was then introduced into the premodified host. The final strain is RR1($\lambda$DE3) [pBR-NspIM, pACYC-T7-NspIR]. This overexpression strain produced approximately $10^5$ units of recombinant NspI per gram of wet E. coli cells.

BRIEF DESCRIPTION OF THE DRAWINGS

FIG. 2 is the DNA sequence (SEQ ID NO:1) of nspIM gene and its predicted amino acid sequence (SEQ ID NO:2).

DETAILED DESCRIPTION OF THE INVENTION

The present invention relates to clones of the NspI restriction and modification genes, as well to the recombinant NspI restriction endonuclease produced from such clones.

The method described herein by which the NspI restriction gene and methylase gene are preferably cloned and expressed includes the following steps:

1. The DNA of Nostoc sp. is purified. This strain is available from American Tissue Type Culture Collection (ATCC 29411).

2. The DNA is digested partially with restriction endonucleases such as ApoI, Tsp509I, or Sau3AI. The DNA is also digested completely with BamHI, BglII, HindIII, PstI, SalI, or XbaI. The ApoI and Tsp509I-digested partial DNA is ligated to EcoRI digested and CIP treated pRRS derivative (this vector contains two NspI sites). The Sau3AI-digested DNA is ligated to BamHI cut and CIP treated PRRS derivative. BamHI, BglII, HindIII, PstI, SalI, or XbaI-digested DNA is ligated to pRRS with compatible ends.

3. The ligated DNA mixture is used to transform an appropriate host such as E. coli RR1 cells. The DNA/cell mixture is plated on ampicillin plates for transformed cells. After incubation, the transformed colonies are collected together into a single culture, the primary cell library. The recombinant plasmids are purified in toto from the primary cell library to make a primary plasmid library.

5. The plasmid library is then digested in vitro with the NspI restriction endonuclease. NspI restriction digestion causes the selective destruction of unmodified, non-methylase-containing, clones, resulting in an increase in the relative frequency of NspI methylase-carrying clones.

6. The digested plasmid library DNA is transformed back into an E. coli host such as RR1, and transformed colonies are again obtained by plating on Amp plates. The colonies are picked and their DNA is analyzed for the presence of the NspI modification in the following manner: The plasmid DNA is purified and incubated in vitro with NspI restriction endonuclease to determine whether it is resistant to digestion by NspI. The DNA of clones that carry the NspI methylase gene should be fully or partially modified and resistant to NspI digestion. One resistant clone is found in the ApoI partial library.

7. Once the resistant clone is identified. The insert DNA is mapped by restriction mapping, subcloned into pUC19 and sequenced using pUC19 universal primers and custom-made primers. Plasmid DNA was sequenced by the dideoxy termination method.

8. After the entire insert is sequenced, the DNA sequence is translated into amino acid sequences. Two open reading frames were found. One ORF contains ten conserved sequence motifs of C5 methylase motifs and was assigned as nspIM gene. the second ORF is a partial reading frame missing the start codon. Inverse PCR primers were made based on the known DNA sequence. The adjacent DNA was amplified by inverse PCR. Inverse PCR products were sequenced. Five additional codons were found with a start codon.

9. Expression of nspIR gene in pRRS: The pRRS plasmid is as described (Skoglund et al, Gene, 88:1–5 (1990)). To construct a premodified host, the nspIM gene was amplified by PCR and inserted in pACYC184, giving rise to plasmid pACYC-NspIM. The nspIR gene was amplified by PCR and ligated to expression vector pRRS. NspI activity was detected in the cell extracts prepared from 10 ml of IPTG-induced cells. This clone is not stable as evidenced by loss of NspI activity in cell extracts prepared from 500 ml cell cultures.

Figure 5:
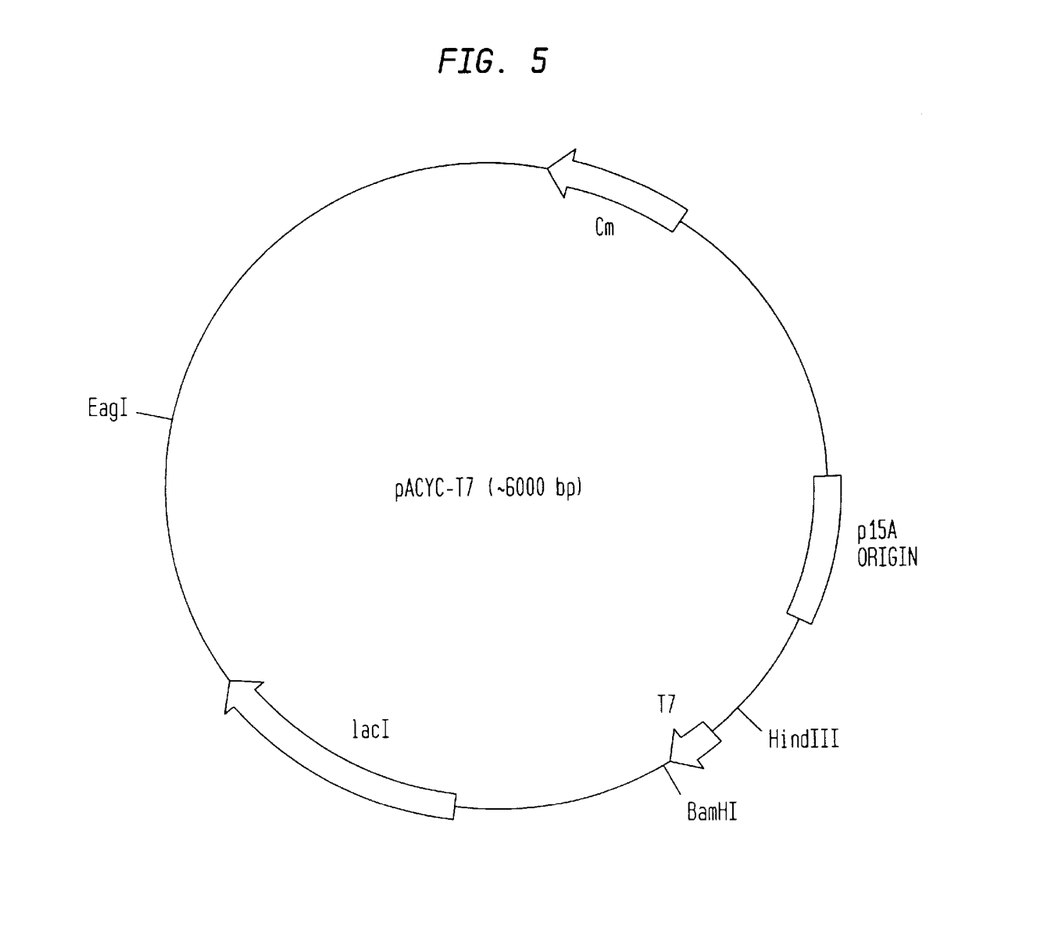
FIG. 5 is a plasmid map of pACYC-T7. The EagI and HindIII fragment was derived from pET-11d. The BamHI site was used for insertion of nspIR gene.

10. Expression of nspIR gene in pACYC-T7: The nspIm gene was inserted into pBR322 to generate pBR-NspIM. E. coli B strain ER2504 was transformed with pBR-NspIM to premodify the host. A low copy number T7 expression vector pACYC-T7 was constructed (see FIG. 5). The nspIR gene was amplified by PCR and inserted into pACYC-T7. The resulting strain is ER2504 [pBR-NspIM, pACYC-T7-NspIR]. This strain produced about $10^4$ to $10^5$ units of NspI under IPTG-induced condition. The strain is not stable. It requires fresh transformation. Cells from −70° C. glycerol stocks yielded low activity. Because the nspIR gene is under a tight T7 promoter control and it is cloned in a low copy plasmid, it was reasoned that the endonuclease gene is probably not the cause of instability. The instability is most likely caused by the M.NspI expression.

11. To construct a stable expression strain, pBR-NspIM was transferred into an *E. coli* K strain RR1(λDE3). The premodified cell RR1 (λDE3) [pBR-NspIM] was then transformed with pACYC-T7-NspIR. The final strain is RR1 (λDE3) [pBR-NspIM, pACYC-T7-NspIR], which produces $10^5$ units of NspI endonuclease per gram of wet *E. coli* cells.

12. Purification of the recombinant NspI: The crude cell extract containing the NspI restriction endonuclease activity is purified by affinity-chromatography and anion exchange chromatography, hydrophobic interaction chromatography. The chromatography steps are consisted of:
 a) Purification of NspI through anion exchange chromatography such as DEAE and pooling the peak fractions containing NspI restriction endonuclease.
 b) Purification of NspI through hydrophobic interaction column such as Phenyl Sepharose® column and pooling the peak fractions containing NspI restriction endonuclease.
 c) Purification of NspI through DNA binding protein affininy column such as Heparin Sepharose® column and pooling the peak fractions containing NspI restriction endonuclease.
 d) Repeat step b (hydrophobic interaction column).
 e) Repeat step c (DNA binding protein affininy column).

After purification through five columns, the recombinant NspI was purified and lacks contaminating exonuclease and non-specific endonuclease.

Although the above-outlined steps represent the preferred mode for practicing the present invention, it will be apparent to those skilled in the art that the above described approach can vary in accordance with techniques known in the art.

The following Examples are given to illustrate embodiments of the present invention as it is presently preferred to be practiced. It will be understood that the examples are illustrative, and that the invention is not to be considered as restricted thereto except as indicated in the appended claims.

The references cited above and below are herein incorporated by reference.

EXAMPLE 1

Cloning of nspIM Gene

1. Construction of a Sau3AI partial genomic DNA library

Genomic DNA was purified from Nostoc sp. This strain is available from American Tissue Type Culture Collection (ATCC 29411). Ten ug of Nostoc sp. genomic DNA was digested partially with restriction endonucleases such as ApoI, Sau3AI or Tsp509I (4, 2, 1, 0.5, 0.25 and 0.125 units for 30 min at the required temperature). Genomic DNA was also digested completely with BamHI, BglII, HindIII, PstI, SalI, or XbaI. The ApoI and Tsp509I-digested partial DNA was ligated to EcoRI digested and CIP treated pRRS derivative (this vector contains two NspI sites). The Sau3AI-digested DNA was ligated to BamHI cut and CIP treated pRRS derivative. BamHI, BglII, HindIII, PstI, SalI, or XbaI-digested DNA was ligated to PRRS with compatible ends. Transformation was carried out by mixing RR1 (TonA$^-$, DnaseI$^-$) competent cells and the ligated DNA by the standard procedure. Transformants were plated on LB agar plus Amp (100 μg/ml). To increase the complexity of the DNA library, RR1 electrocompetent cells were also prepared and the ligated DNA was dialyzed by drop dialysis and then used for electroporation. About 50,000 colonies were obtained in transformation and electroporation. All the transformants were pooled and inoculated into 2 liters of LB broth plus Amp and incubated at 37° C. overnight. Plasmid DNA was prepared from the overnight cells by Qiagen midi and maxi columns.

2. Challenge ApoI, Sau3AI, and Tsp509I partial DNA libraries with NspI digestion and cloning of NspI methylase gene 0.2, 0.5 and 1 μg of the ApoI, Sau3AI, and Tsp509I partial library DNA was digested with 25 units of NspI at 37° C. overnight. The digested DNA was used to retransform RR1 (TonA$^-$, DnaseI$^-$) competent cells. Approximately 200 transformants were obtained in each challenged library. Mini-preparation of plasmid DNA was isolated from 2 ml cell culture of 36 transformants for each challanged DNA. Individual plasmid DNA was digested with NspI to detect any resistance to digestion. One plasmid isolate #36 from the ApoI partial library displayed resistance to NspI digestion.

The insert was mapped by restriction mapping. Three deletion clones (EcoRI fragment deletion, XbaI fragment deletion, BsAI-PstI fragment deletion) were constructed. The EcoRI, HindIII, MfeI, and XbaI fragments were subcloned in pUC19. The original insert and subclone inserts were sequenced using universal primers and custom-made primers. After the entire insert was sequenced, the DNA sequence was translated into amino acid sequences. One open reading frame and a partial ORF were found. One ORF contains the typical ten conserved sequence motifs of C5 methylase and was assigned as nspIM gene. The nspIM gene sequence is shown in FIG. 2. The second ORF is a partial reading frame (718 bp) missing a start codon. In example 2, it was demonstrated that this partial ORF contains the majority of nspIR gene.

EXAMPLE 2

Cloning of nspIR Gene

Inverse PCR primers were made based on the known DNA sequence of the partial reading frame. The primers have the following sequences:

5' CTGAACTGGCTCTGAATTGTCTGTACT 3' (160-09) (SEQ ID NO:5)

5' CAAGTCTTTAAGCTGTTGTCAGATCAA 3' (160-10) (SEQ ID NO:6)

Figure 1:
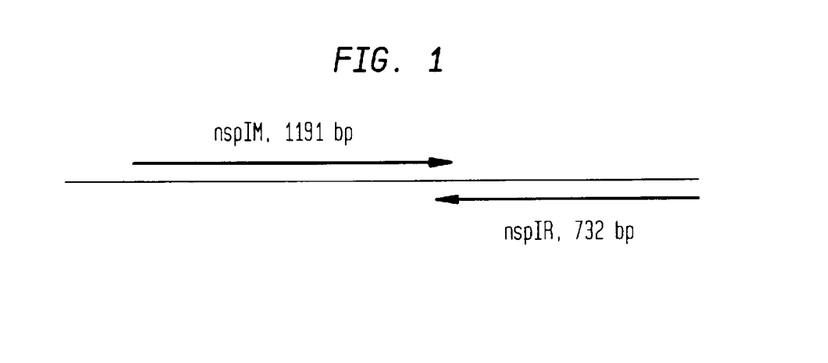
FIG. 1 illustrates the gene organization of NspI restriction-modification system.
Figure 3:
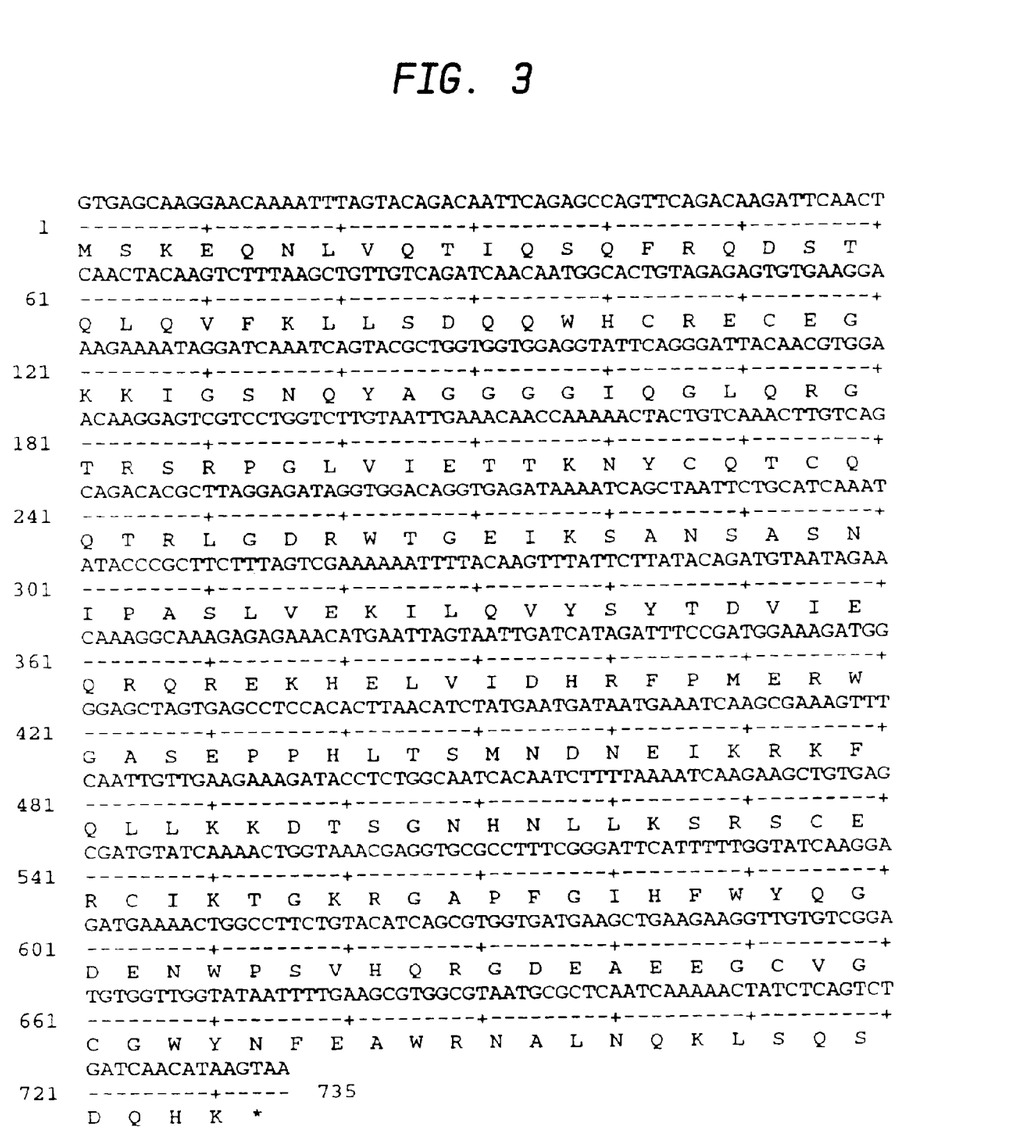
FIG. 3 is the DNA sequence (SEQ ID NO:3) of nspIR gene and its predicted amino acid sequence (SEQ ID NO:4).
Figure 4:
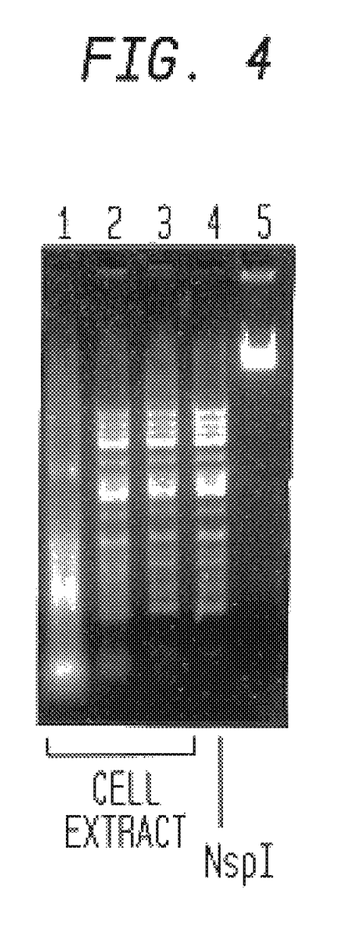
FIG. 4 is a photograph of NspI restriction enzyme activity from E. coli cell extract. Lane 1, 2, and 3, digestion of $\lambda$DNA with 10-, 100-, and 1000-fold dilution of cell extract, respectively; lane 4, positive control, NspI digestion of $\lambda$DNA; lane 5, uncut $\lambda$DNA.

Nostoc sp. genomic DNA was cleaved with AciI, AluI, BfaI, BssKI, BstNI, DdeI, DraI, HhaI, HinPI, MboII, MfeI, MseI, NlaIII, RsaI, Sau3AI, ScrFI, SfcI, TaiI, TaqI, or Tsp509I, respectively. The restriction enzyme cleaved DNA was self-ligated at a low concentration (2 μg/ml) and the self-ligated circular molecules were used as templates in inverse PCR using a set of primers 160-09 and 160-10. Inverse PCR conditions were 95° C. 1' 55° C. 1', 72° C. 2', for 30 cycles. Inverse PCR products were found in AciI, BfaI, DdeI, DraI, HhaI, HinPI, MboII, MfeI, and Sau3AI cleaved and self-ligated DNA. AciI, DraI, HhaI, HinPI, and MfeI inverse PCR products were gel-purified and cloned in pUC19 and sequenced. Five additional codons were found upstream with a start codon. The DNA sequence is shown in FIG. 3. This entire ORF is 732 bp and was demonstrated in example 3 that this ORF is the nspIR gene.

EXAMPLE 3

Expression of NspI Restriction Endonuclease Using PRRS Vector in *E. coli*

Two primers were synthesized and used to amplify the nspIM gene from Nostoc sp. genomic DNA. The primer sequences were:

5' CAAGGATCCGGAGGTTAATTAAATG-CAAGGTACACAACTTTCTTTTTTAG 3' (161-78) (SEQ ID NO:7)

5' CGCGGATCCTCAATCAAAAACTATCT-CAGTCTGATCAACATA 3' (161-80) (SEQ ID NO:8)

PCR conditions were 5 units Taq plus vent® DNA polymerase, 94° C. 1', 55° C. 1', and 72° C. 1' for 20 cycles.

The nspIM gene PCR DNA was digested with BamHI and ligated to BamHI digested and CIP-treated pACYC184. The resulting plasmid is pACYC-NspIM. M.NspI fully modifies the NspI sites in the plasmid as evidenced by the complete resistance to NspI digestion.

Two primers were synthesized and used to amplify the nspIR gene from Nostoc sp. genomic DNA. The primer sequences were:

5' CAAGGATCCGGAGGTTTAATAATGAG-CAAGGAACAAAATTTAGTACAGACA 3' (162-65) (SEQ ID NO:9)

5' CAAGGATCCTTACTTATGTTGATCA-GACTGAGATAG 3' (162-66) (SEQ ID NO:10)

Nostoc sp. cells were boiled for 5 min to release genomic DNA. This DNA sample was used for PCR amplification of the nspIR gene. PCR conditions were 5 units Taq plus Vent® DNA polymerase (50:1 ratio), 94° C. 1', 55° C. 1', and 72° C. 1' for 30 cycles. The PCR DNA was purified and digested with BamHI. The PCR DNA was purified again and ligated to BamHI digested and CIP treated pRRS. The ligated DNA was used to transform ER2426 [pACYC-NspIM]. After screening 72 plasmids, 16 isolate were found to carry the desired insert. Cell extracts were prepared from eight 10-ml overnight cells and assayed for NspI endonuclease activity. #16 and #17 displayed high NspI activity. When these two clones were amplified in 500 ml overnight cultures, NspI activity was not detected in the cell extract. It was concluded that the NspI overproducing clone is not stable. Efforts were made to express nspIR gene in a low copy number plasmid as described in Example 4.

EXAMPLE 4
Expression of NspI Restriction Endonuclease Using a Low Copy Number T7 Expression Vector pACYC-T7

The BamHI fragment containing nspIM gene was digested from pACYC-NspIM and gel-purified. This fragment was ligated to BamHI digested and CIP-treated pBR322. The resulting plasmid is pBR-NspIM. M.NspI fully modifies NspI sites on plasmid in vivo.

To construct a stable NspI overexpression clone, a low-copy number T7 expression vector was first constructed. The EagI-HindIII fragment was purified from pET11d and ligated to EagI and HindIII-digested pACYC184. The resulting plasmid pACYC-T7 contains p15A origin, lacI gene, and Cm$^R$ selection marker (see FIG. 5). Nostoc sp. cells were boiled for 5 min to release genomic DNA. This DNA sample was used for PCR amplification of the nspIR gene. PCR conditions were 0.24 ug of primers 162-65 and 162-66, 5 units Taq plus Vent® DNA polymerase (50:1 ratio), 94° C. 1', 55° C. 1', and 72° C. 1' for 30 cycles. The PCR DNA was purified and digested with BamHI. The PCR DNA was purified again and ligated to BamHI digested and CIP treated pACYC-T7. The ligated DNA was transformed into ER2504 [pBR-NspIM]. After screening 72 plasmid isolates, 15 isolates were found to contain the correct size insert. 10 ml cell cultures were induced with IPTG at 0.5 mM final concentration. #41 and #48 were found to produce high NspI activity. However, the overexpression strain ER2504 [pBR-NspIM, pACYC-T7-NspIR] is not stable. It required fresh transformation at the beginning of each large fermentation (100 Liters). Cells grown from −70° C. glycerol stock produced at least 10-fold less NspI than the cells derived from fresh transformation.

EXAMPLE 5
Expression of NspI in the *E. coli* K Strain RR1 (λDE3) and Purification of NspI Restriction Endonuclease Because the nspIR gene is under a tight T7 promoter control and it is cloned in a low copy plasmid, it is reasoned that the NspI endonuclease is probably not the cause of instability. The instability is most likely caused by the M.NspI expression. To construct a stable expression strain, pBR-NspIM was transferred into an *E. coli* K strain RR1 (λDE3). RR1(λDE3) strain was constructed by William Jack and Julia Menin (New England Biolabs, Inc.). The premodified cell RR1 (kDE3) [pBR-NspIM] was then transformed with pACYC-T7-NspIR. The final strain is RR1 (λDE3) [pBR-NspIM, pACYC-T7-NspIR], which produces $10^5$ units of NspI endonuclease per gram of wet *E. coli* cells after IPTG induction. This K strain is more stable than the T7 expression B strain.

Purification of the recombinant NspI: The crude cell extract containing the NspI restriction endonuclease activity is purified by affinity-chromatography and anion exchange chromatography, hydrophobic interaction chromatography. The chromatography steps were consisted of:

a) Purification of NspI through anion exchanger chromatography such as DEAE and pooling the peak fractions containing NspI restriction endonuclease.

b) Purification of NspI through hydrophobic interaction column such as Phenyl Sepharose® column and pooling the peak fractions containing NspI restriction endonuclease.

c) Purification of NspI through DNA binding protein affininy column such as Heparin Sepharose® column and pooling the peak fractions containing NspI restriction endonuclease.

d) Repeat step b (hydrophobic interaction column).

e) Repeat step c (DNA binding protein affininy column)

After purification through five columns, the recombinant NspI was purified and lacks any contaminating exonuclease and non-specific endonuclease.

*E. coli* RR1 (λDE) [pBR-NspIM, pACYC-T7-NspIR] strain has been deposited with the American Type Culture Collection on Aug. 13, 1998 and received Accession No. 98836.

What is claimed is:

1. Isolated DNA coding for the NspI restriction endonuclease, wherein the isolated DNA is obtainable from Nostoc sp. (ATCC 29411).

2. A recombinant DNA vector comprising a vector into which a DNA segment encoding the NspI restriction endonuclease has been inserted.

3. Isolated DNA encoding the NspI restriction endonuclease and methylase, wherein the isolated DNA is obtainable from ATCC No. 98836.

4. A cloning vector which comprises the isolated DNA of claim 3.

5. A host cell transformed by the vector of claims 2 or 4.

6. A method of producing NspI restriction endonuclease comprising culturing a host cell transformed with the vector of claim 2 or 4 under conditions suitable for expression of said endonuclease.

* * * * *

UNITED STATES PATENT AND TRADEMARK OFFICE
CERTIFICATE OF CORRECTION

PATENT NO. : 6,027,929  
DATED : February 22, 2000  
INVENTOR(S) : Xu, et. al.

Page 1 of 2

It is certified that error appears in the above-identified patent and that said Letters Patent is hereby corrected as shown below:

Column 3, line 64, replace "digested" with --digested--

Column 4, line 4, replace "mixtur e" with --mixture--

Column 4, line 53, replace "nspIm" with --nspIM--

Column 5, line 55, replace "PRRS" with --pRRS--

Column 6, line 56, replace "PRRS" with --pRRS--

Column 8, line 23, replace "(kDE3)" with --($\lambda$DE3)--

UNITED STATES PATENT AND TRADEMARK OFFICE
CERTIFICATE OF CORRECTION

PATENT NO. : 6,027,929
DATED : February 22, 2000
INVENTOR(S) : Xu, et. al.

It is certified that error appears in the above-identified patent and that said Letters Patent is hereby corrected as shown below:

Column 4, line 37, replace "gene. the" with --gene. The--

Column 5, line 20, replace "affininy" with --affinity--

Column 5, line 25, replace "affininy" with --affinity--

Column 8, line 22, replace "Julia" with --Julie--

Column 8, line 41, replace "affininy" with --affinity--

Column 8, line 45, replace "affininy" with --affinity--

Signed and Sealed this

Fourteenth Day of November, 2000

Attest:

Q. TODD DICKINSON

*Attesting Officer*        *Director of Patents and Trademarks*

SEQUENCE LISTING

```
<160> NUMBER OF SEQ ID NOS: 10

<210> SEQ ID NO 1
<211> LENGTH: 1194
<212> TYPE: DNA
<213> ORGANISM: Nostoc sp.
<220> FEATURE:
<221> NAME/KEY: CDS
<222> LOCATION: (1)..(1191)
```

<400> SEQUENCE: 1

| | | | | | | | | | | | | | | | | |
|---|---|---|---|---|---|---|---|---|---|---|---|---|---|---|---|---|
| atg | caa | ggt | aca | caa | ctt | tct | ttt | ttt | agc | aac | gaa | gaa | ggg | ttt | aat | 48 |
| Met | Gln | Gly | Thr | Gln | Leu | Ser | Phe | Phe | Ser | Asn | Glu | Glu | Gly | Phe | Asn | |
| 1 | | | | 5 | | | | | 10 | | | | | 15 | | |
| cct | acc | aaa | aag | gag | aaa | aaa | cca | aaa | tta | gga | cgt | tat | gaa | cgt | atc | 96 |
| Pro | Thr | Lys | Lys | Glu | Lys | Lys | Pro | Lys | Leu | Gly | Arg | Tyr | Glu | Arg | Ile | |
| | | | 20 | | | | | 25 | | | | | 30 | | | |
| aaa | cgt | aat | tta | gag | aaa | aat | gat | caa | gat | cca | tac | aag | ata | ttt | att | 144 |
| Lys | Arg | Asn | Leu | Glu | Lys | Asn | Asp | Gln | Asp | Pro | Tyr | Lys | Ile | Phe | Ile | |
| | | 35 | | | | | 40 | | | | | 45 | | | | |
| gat | gtt | aat | acc | cca | cta | ata | cca | gca | tct | caa | tat | act | ttt | gtg | gat | 192 |
| Asp | Val | Asn | Thr | Pro | Leu | Ile | Pro | Ala | Ser | Gln | Tyr | Thr | Phe | Val | Asp | |
| 50 | | | | | 55 | | | | | 60 | | | | | | |
| ctg | ttc | tgt | ggt | gca | gga | gga | att | aca | caa | gga | tta | gta | cag | gct | gga | 240 |
| Leu | Phe | Cys | Gly | Ala | Gly | Gly | Ile | Thr | Gln | Gly | Leu | Val | Gln | Ala | Gly | |
| 65 | | | | | 70 | | | | | 75 | | | | | 80 | |
| ttc | cag | gcc | tta | gct | agt | gtg | gaa | att | agt | cca | att | gct | tct | gct | aca | 288 |
| Phe | Gln | Ala | Leu | Ala | Ser | Val | Glu | Ile | Ser | Pro | Ile | Ala | Ser | Ala | Thr | |
| | | | | 85 | | | | | 90 | | | | | 95 | | |
| cat | caa | aga | aat | ttt | cct | cat | tgt | cat | cat | ttt | tgg | gga | gat | ata | gaa | 336 |
| His | Gln | Arg | Asn | Phe | Pro | His | Cys | His | His | Phe | Trp | Gly | Asp | Ile | Glu | |
| | | | 100 | | | | | 105 | | | | | 110 | | | |
| caa | ttt | tat | cca | aaa | agt | tgg | ttg | caa | caa | att | ggc | tat | cct | gaa | gta | 384 |
| Gln | Phe | Tyr | Pro | Lys | Ser | Trp | Leu | Gln | Gln | Ile | Gly | Tyr | Pro | Glu | Val | |
| | | 115 | | | | | 120 | | | | | 125 | | | | |
| aat | ctg | gtg | gtt | ggt | ggt | cct | cct | tgt | cag | ggg | ttt | tcg | gta | gca | ggt | 432 |
| Asn | Leu | Val | Val | Gly | Gly | Pro | Pro | Cys | Gln | Gly | Phe | Ser | Val | Ala | Gly | |
| | 130 | | | | | 135 | | | | | 140 | | | | | |
| aaa | cgc | gat | ccc | aaa | gat | ccg | cgt | aat | cgt | cta | ttt | tat | gaa | ttt | gta | 480 |
| Lys | Arg | Asp | Pro | Lys | Asp | Pro | Arg | Asn | Arg | Leu | Phe | Tyr | Glu | Phe | Val | |
| 145 | | | | | 150 | | | | | 155 | | | | | 160 | |
| cgt | gtg | gta | tca | gaa | ata | cgt | ccg | tgg | tat | gta | gtt | atg | gaa | aat | gta | 528 |
| Arg | Val | Val | Ser | Glu | Ile | Arg | Pro | Trp | Tyr | Val | Val | Met | Glu | Asn | Val | |
| | | | | 165 | | | | | 170 | | | | | 175 | | |
| cca | gga | att | cta | acc | att | caa | aat | gga | aat | gtg | aag | caa | gct | att | att | 576 |
| Pro | Gly | Ile | Leu | Thr | Ile | Gln | Asn | Gly | Asn | Val | Lys | Gln | Ala | Ile | Ile | |
| | | | 180 | | | | | 185 | | | | | 190 | | | |
| gaa | gct | ttt | gaa | tct | att | ggt | tat | cct | cat | gtt | tct | gta | gca | att | cta | 624 |
| Glu | Ala | Phe | Glu | Ser | Ile | Gly | Tyr | Pro | His | Val | Ser | Val | Ala | Ile | Leu | |
| | | 195 | | | | | 200 | | | | | 205 | | | | |
| gaa | tct | gct | gac | tat | gga | gta | cca | cag | att | aga | cca | aga | gct | atc | ttt | 672 |
| Glu | Ser | Ala | Asp | Tyr | Gly | Val | Pro | Gln | Ile | Arg | Pro | Arg | Ala | Ile | Phe | |
| | 210 | | | | | 215 | | | | | 220 | | | | | |
| att | gct | aat | aga | ttc | gga | atg | cca | aat | cca | tat | cct | aaa | gct | cag | tta | 720 |
| Ile | Ala | Asn | Arg | Phe | Gly | Met | Pro | Asn | Pro | Tyr | Pro | Lys | Ala | Gln | Leu | |
| 225 | | | | | 230 | | | | | 235 | | | | | 240 | |
| tta | cca | gaa | gaa | tat | aaa | ccc | atc | gaa | tca | gct | att | tct | gat | tta | cca | 768 |
| Leu | Pro | Glu | Glu | Tyr | Lys | Pro | Ile | Glu | Ser | Ala | Ile | Ser | Asp | Leu | Pro | |
| | | | | 245 | | | | | 250 | | | | | 255 | | |
| gaa | tat | act | cca | att | cca | gaa | att | aat | cac | caa | tgg | act | aga | cat | tca | 816 |
| Glu | Tyr | Thr | Pro | Ile | Pro | Glu | Ile | Asn | His | Gln | Trp | Thr | Arg | His | Ser | |
| | | | 260 | | | | | 265 | | | | | 270 | | | |
| cca | gag | tat | atg | gag | cgt | att | gca | aaa | gta | ccc | cct | ggt | ggt | tct | tta | 864 |
| Pro | Glu | Tyr | Met | Glu | Arg | Ile | Ala | Lys | Val | Pro | Pro | Gly | Gly | Ser | Leu | |
| | | 275 | | | | | 280 | | | | | 285 | | | | |
| tat | caa | aaa | tat | gtt | gat | gcc | ttt | aag | cgt | caa | tat | cca | ggt | aaa | cca | 912 |
| Tyr | Gln | Lys | Tyr | Val | Asp | Ala | Phe | Lys | Arg | Gln | Tyr | Pro | Gly | Lys | Pro | |
| | 290 | | | | | 295 | | | | | 300 | | | | | |

```
agt atg act gtt aaa gaa aat cat ggc ggt act cat atc cac cca tat      960
Ser Met Thr Val Lys Glu Asn His Gly Gly Thr His Ile His Pro Tyr
305                 310                 315                 320 tta aat cgg gta att tca tct cgt gag atg gca aga tta caa agc ttt     1008
Leu Asn Arg Val Ile Ser Ser Arg Glu Met Ala Arg Leu Gln Ser Phe
                325                 330                 335 cct gat tca ttc att ttt gaa ggg act atg aaa aaa gcc atg tgg caa     1056
Pro Asp Ser Phe Ile Phe Glu Gly Thr Met Lys Lys Ala Met Trp Gln
            340                 345                 350 att ggg aat gca gtc cca cct cgt tta gca gag tgt att ggt tat gcg     1104
Ile Gly Asn Ala Val Pro Pro Arg Leu Ala Glu Cys Ile Gly Tyr Ala
        355                 360                 365 ctc ata cct tat tta aac aag att gca ctt aac act gat cat caa gtt     1152
Leu Ile Pro Tyr Leu Asn Lys Ile Ala Leu Asn Thr Asp His Gln Val
    370                 375                 380 gat att act tat gtt gat cag act gag ata gtt ttt gat tga             1194
Asp Ile Thr Tyr Val Asp Gln Thr Glu Ile Val Phe Asp
385                 390                 395
```

<210> SEQ ID NO 2
<211> LENGTH: 397
<212> TYPE: PRT
<213> ORGANISM: Nostoc sp.

<400> SEQUENCE: 2

```
Met Gln Gly Thr Gln Leu Ser Phe Phe Ser Asn Glu Glu Gly Phe Asn
1               5                   10                  15

Pro Thr Lys Lys Glu Lys Lys Pro Lys Leu Gly Arg Tyr Glu Arg Ile
            20                  25                  30

Lys Arg Asn Leu Glu Lys Asn Asp Gln Asp Pro Tyr Lys Ile Phe Ile
        35                  40                  45

Asp Val Asn Thr Pro Leu Ile Pro Ala Ser Gln Tyr Thr Phe Val Asp
    50                  55                  60

Leu Phe Cys Gly Ala Gly Gly Ile Thr Gln Gly Leu Val Gln Ala Gly
65                  70                  75                  80

Phe Gln Ala Leu Ala Ser Val Glu Ile Ser Pro Ile Ala Ser Ala Thr
                85                  90                  95

His Gln Arg Asn Phe Pro His Cys His His Phe Trp Gly Asp Ile Glu
            100                 105                 110

Gln Phe Tyr Pro Lys Ser Trp Leu Gln Gln Ile Gly Tyr Pro Glu Val
        115                 120                 125

Asn Leu Val Val Gly Pro Pro Cys Gln Gly Phe Ser Val Ala Gly
    130                 135                 140

Lys Arg Asp Pro Lys Asp Pro Arg Asn Arg Leu Phe Tyr Glu Phe Val
145                 150                 155                 160

Arg Val Val Ser Glu Ile Arg Pro Trp Tyr Val Val Met Glu Asn Val
                165                 170                 175

Pro Gly Ile Leu Thr Ile Gln Asn Gly Asn Val Lys Gln Ala Ile Ile
            180                 185                 190

Glu Ala Phe Glu Ser Ile Gly Tyr Pro His Val Ser Val Ala Ile Leu
        195                 200                 205

Glu Ser Ala Asp Tyr Gly Val Pro Gln Ile Arg Pro Arg Ala Ile Phe
    210                 215                 220

Ile Ala Asn Arg Phe Gly Met Pro Asn Pro Tyr Pro Lys Ala Gln Leu
225                 230                 235                 240

Leu Pro Glu Glu Tyr Lys Pro Ile Glu Ser Ala Ile Ser Asp Leu Pro
                245                 250                 255
```

```
                            Glu Tyr Thr Pro Ile Pro Glu Ile Asn His Gln Trp Thr Arg His Ser
                                        260                 265                 270

Pro Glu Tyr Met Glu Arg Ile Ala Lys Val Pro Pro Gly Gly Ser Leu
                                    275                 280                 285

Tyr Gln Lys Tyr Val Asp Ala Phe Lys Arg Gln Tyr Pro Gly Lys Pro
                                290                 295                 300

Ser Met Thr Val Lys Glu Asn His Gly Gly Thr His Ile His Pro Tyr
                            305                 310                 315                 320

Leu Asn Arg Val Ile Ser Ser Arg Glu Met Ala Arg Leu Gln Ser Phe
                                            325                 330                 335

Pro Asp Ser Phe Ile Phe Glu Gly Thr Met Lys Lys Ala Met Trp Gln
                                        340                 345                 350

Ile Gly Asn Ala Val Pro Pro Arg Leu Ala Glu Cys Ile Gly Tyr Ala
                                    355                 360                 365

Leu Ile Pro Tyr Leu Asn Lys Ile Ala Leu Asn Thr Asp His Gln Val
                                370                 375                 380

Asp Ile Thr Tyr Val Asp Gln Thr Glu Ile Val Phe Asp
                            385                 390                 395

<210> SEQ ID NO 3
                            <211> LENGTH: 735
                            <212> TYPE: DNA
                            <213> ORGANISM: Nostoc sp.
                            <220> FEATURE:
                            <221> NAME/KEY: CDS
                            <222> LOCATION: (1)..(732)

<400> SEQUENCE: 3 gtg agc aag gaa caa aat tta gta cag aca att cag agc cag ttc aga        48
                            Met Ser Lys Glu Gln Asn Leu Val Gln Thr Ile Gln Ser Gln Phe Arg
                             1               5                  10                  15 caa gat tca act caa cta caa gtc ttt aag ctg ttg tca gat caa caa      96
                            Gln Asp Ser Thr Gln Leu Gln Val Phe Lys Leu Leu Ser Asp Gln Gln
                                            20                  25                  30 tgg cac tgt aga gag tgt gaa gga aag aaa ata gga tca aat cag tac    144
                            Trp His Cys Arg Glu Cys Glu Gly Lys Lys Ile Gly Ser Asn Gln Tyr
                                        35                  40                  45 gct ggt ggt gga ggt att cag gga tta caa cgt gga aca agg agt cgt    192
                            Ala Gly Gly Gly Gly Ile Gln Gly Leu Gln Arg Gly Thr Arg Ser Arg
                                50                  55                  60 cct ggt ctt gta att gaa aca acc aaa aac tac tgt caa act tgt cag    240
                            Pro Gly Leu Val Ile Glu Thr Thr Lys Asn Tyr Cys Gln Thr Cys Gln
                            65                  70                  75                  80 cag aca cgc tta gga gat agg tgg aca ggt gag ata aaa tca gct aat    288
                            Gln Thr Arg Leu Gly Asp Arg Trp Thr Gly Glu Ile Lys Ser Ala Asn
                                            85                  90                  95 tct gca tca aat ata ccc gct tct tta gtc gaa aaa att tta caa gtt    336
                            Ser Ala Ser Asn Ile Pro Ala Ser Leu Val Glu Lys Ile Leu Gln Val
                                        100                 105                 110 tat tct tat aca gat gta ata gaa caa agg caa aga gag aaa cat gaa    384
                            Tyr Ser Tyr Thr Asp Val Ile Glu Gln Arg Gln Arg Glu Lys His Glu
                                    115                 120                 125 tta gta att gat cat aga ttt ccg atg gaa aga tgg gga gct agt gag    432
                            Leu Val Ile Asp His Arg Phe Pro Met Glu Arg Trp Gly Ala Ser Glu
                                130                 135                 140 cct cca cac tta aca tct atg aat gat aat gaa atc aag cga aag ttt    480
                            Pro Pro His Leu Thr Ser Met Asn Asp Asn Glu Ile Lys Arg Lys Phe
                            145                 150                 155                 160
```

```
caa ttg ttg aag aaa gat acc tct ggc aat cac aat ctt tta aaa tca        528
Gln Leu Leu Lys Lys Asp Thr Ser Gly Asn His Asn Leu Leu Lys Ser
            165                 170                 175 aga agc tgt gag cga tgt atc aaa act ggt aaa cga ggt gcg cct ttc        576
Arg Ser Cys Glu Arg Cys Ile Lys Thr Gly Lys Arg Gly Ala Pro Phe
        180                 185                 190 ggg att cat ttt tgg tat caa gga gat gaa aac tgg cct tct gta cat        624
Gly Ile His Phe Trp Tyr Gln Gly Asp Glu Asn Trp Pro Ser Val His
            195                 200                 205 cag cgt ggt gat gaa gct gaa gaa ggt tgt gtc gga tgt ggt tgg tat        672
Gln Arg Gly Asp Glu Ala Glu Glu Gly Cys Val Gly Cys Gly Trp Tyr
        210                 215                 220 aat ttt gaa gcg tgg cgt aat gcg ctc aat caa aaa cta tct cag tct        720
Asn Phe Glu Ala Trp Arg Asn Ala Leu Asn Gln Lys Leu Ser Gln Ser
225                 230                 235                 240 gat caa cat aag taa                                                    735
Asp Gln His Lys <210> SEQ ID NO 4
<211> LENGTH: 244
<212> TYPE: PRT
<213> ORGANISM: Nostoc sp.

<400> SEQUENCE: 4

Met Ser Lys Glu Gln Asn Leu Val Gln Thr Ile Gln Ser Gln Phe Arg
 1               5                  10                  15

Gln Asp Ser Thr Gln Leu Gln Val Phe Lys Leu Leu Ser Asp Gln Gln
            20                  25                  30

Trp His Cys Arg Glu Cys Glu Gly Lys Lys Ile Gly Ser Asn Gln Tyr
        35                  40                  45

Ala Gly Gly Gly Ile Gln Gly Leu Gln Arg Gly Thr Arg Ser Arg
    50                  55                  60

Pro Gly Leu Val Ile Glu Thr Thr Lys Asn Tyr Cys Gln Thr Cys Gln
65                  70                  75                  80

Gln Thr Arg Leu Gly Asp Arg Trp Thr Gly Glu Ile Lys Ser Ala Asn
                85                  90                  95

Ser Ala Ser Asn Ile Pro Ala Ser Leu Val Glu Lys Ile Leu Gln Val
            100                 105                 110

Tyr Ser Tyr Thr Asp Val Ile Glu Gln Arg Gln Arg Glu Lys His Glu
        115                 120                 125

Leu Val Ile Asp His Arg Phe Pro Met Glu Arg Trp Gly Ala Ser Glu
    130                 135                 140

Pro Pro His Leu Thr Ser Met Asn Asp Asn Glu Ile Lys Arg Lys Phe
145                 150                 155                 160

Gln Leu Leu Lys Lys Asp Thr Ser Gly Asn His Asn Leu Leu Lys Ser
                165                 170                 175

Arg Ser Cys Glu Arg Cys Ile Lys Thr Gly Lys Arg Gly Ala Pro Phe
            180                 185                 190

Gly Ile His Phe Trp Tyr Gln Gly Asp Glu Asn Trp Pro Ser Val His
        195                 200                 205

Gln Arg Gly Asp Glu Ala Glu Glu Gly Cys Val Gly Cys Gly Trp Tyr
    210                 215                 220

Asn Phe Glu Ala Trp Arg Asn Ala Leu Asn Gln Lys Leu Ser Gln Ser
225                 230                 235                 240

Asp Gln His Lys
```

-continued

```
<210> SEQ ID NO 5
<211> LENGTH: 27
<212> TYPE: DNA
<213> ORGANISM: Nostoc sp.

<400> SEQUENCE: 5
ctgaactggc tctgaattgt ctgtact                                            27

<210> SEQ ID NO 6
<211> LENGTH: 27
<212> TYPE: DNA
<213> ORGANISM: Nostoc sp.

<400> SEQUENCE: 6
caagtcttta agctgttgtc agatcaa                                            27

<210> SEQ ID NO 7
<211> LENGTH: 52
<212> TYPE: DNA
<213> ORGANISM: Nostoc sp.

<400> SEQUENCE: 7
caaggatccg gaggttaatt aaatgcaagg tacacaactt tctttttta cg                 52

<210> SEQ ID NO 8
<211> LENGTH: 42
<212> TYPE: DNA
<213> ORGANISM: Nostoc sp.

<400> SEQUENCE: 8
cgcggatcct caatcaaaaa ctatctcagt ctgatcaaca ta                           42

<210> SEQ ID NO 9
<211> LENGTH: 51
<212> TYPE: DNA
<213> ORGANISM: Nostoc sp.

<400> SEQUENCE: 9
caaggatccg gaggtttaat aatgagcaag gaacaaaatt tagtacagac a                 51

<210> SEQ ID NO 10
<211> LENGTH: 36
<212> TYPE: DNA
<213> ORGANISM: Nostoc sp.

<400> SEQUENCE: 10
caaggatcct tacttatgtt gatcagactg agatag                                  36
```